United States Patent [19]

Hurst et al.

[11] 4,442,354
[45] Apr. 10, 1984

[54] SPUTTER INITIATED RESONANCE IONIZATION SPECTROMETRY

[75] Inventors: G. Samuel Hurst; James E. Parks; Harold W. Schmitt, all of Oak Ridge, Tenn.

[73] Assignee: Atom Sciences, Inc., Oak Ridge, Tenn.

[21] Appl. No.: 341,895

[22] Filed: Jan. 22, 1982

[51] Int. Cl.³ ............................................. B01D 59/44
[52] U.S. Cl. .................................... 250/281; 250/288; 250/423 P
[58] Field of Search ............... 250/281, 282, 283, 288, 250/423 P

[56] References Cited

U.S. PATENT DOCUMENTS

| | | | |
|---|---|---|---|
| 3,859,226 | 1/1975 | Schillalies | 250/282 |
| 3,953,732 | 4/1976 | Oron | 250/287 |
| 3,955,090 | 5/1976 | Astley et al. | 250/423 P |
| 3,987,302 | 10/1976 | Hurst et al. | 250/423 P |
| 4,070,580 | 1/1978 | Gallagher et al. | 250/423 P |
| 4,302,676 | 11/1981 | Levin et al. | 250/423 P |
| 4,365,157 | 12/1982 | Unsöld et al. | 250/287 |

Primary Examiner—Bruce C. Anderson
Attorney, Agent, or Firm—Poitts, Ruderman & Kesterson

[57] ABSTRACT

Apparatus and method are described for the quantitative analysis of a specific specie within a sample. The analysis has sufficient sensitivity for the detection of as little as one atom of the desired species. The method is accomplished by bombarding a sample with a highly focused charged particle beam; for example, a beam of positive argon ions having an energy from five to thirty kilovolts and a current of one milliampere or greater. This beam impinging upon the sample creates a cloud including secondary ions and neutral particles of the constituents of the sample. The cloud is irradiated with a laser beam having selected wavelengths therein for the unique ionization of the desired specie by means of resonance ionization spectroscopy (RIS). In most applications some energy and/or mass discrimination is required. The energy discrimination can be accomplished by passing the RIS ions through an energy filter, with the ions emanating therefrom having a narrow range of energy. Then, if desired, a mass discrimination may be accomplished in an appropriate mass analyzer such as a time of flight spectrometer, an r.f. quadrupole mass spectrometer or a magnetic sector mass spectrometer.

32 Claims, 12 Drawing Figures

Z = ATOMIC NUMBER = CONSTANT
A = ATOMIC MASS
λ = WAVE LENGTH OF LASER = CONSTANT

A = ATOMIC MASS = VARIABLE
Z = ATOMIC NUMBER = VARIABLE
λ = WAVE LENGTH OF LASER = VARIABLE (Z)

SPUTTER INITIATED RESONANCE IONIZATION SPECTROMETRY

DESCRIPTION

Technical Field

This invention relates generally to high sensitivity analytical techniques and more particularly to a quantitative measurement of the concentration of specific constituents in samples. It is sufficiently sensitive that one atom of a specific constituent of a material may be determined.

Background Art

There are several methods known in the art for determining the concentration of a specific element in samples with relatively high sensitivity. One such method is known as resonance ionization spectroscopy, usually abbreviated as RIS. This method is described, for example, in U.S. Pat. No. 3,987,302 issued to G. S. Hurst, Marvin G. Payne, and E. B. Wagner on Oct. 19, 1976, which is incorporated herein by reference. This RIS method, and improvements thereon, is also described in several publications including an article entitled "Counting the Atoms" in the journal *Physics Today*, September 1980. This article is also incorporated herein by reference. Nearly all atoms of the periodic chart can be analyzed using RIS; however, the sample must be in the gaseous phase for this method of analysis. This RIS method has the potential of determining one atom of a selected constituent in a sample.

Another sensitive and selective analytical method is known as secondary ion mass spectrometry, normally abbreviated as SIMS. This method is described, for example, in National Bureau of Standards Special Publication No. 427, distributed by the U. S. Department of Commerce on October, 1975. It is the printed proceedings of a workshop on SIMS and ion microprobe mass analysis, and is edited by K.F.J. Heinrich and D.E. Newbury. In general, the SIMS method involves the bombardment of a sample with relatively energetic ions and then measuring the secondary ions emanating from the sample. In order to achieve any selectivity, these secondary ions are subjected to mass analysis so that the ions of a specific mass corresponding to the desired atom are determined. Such methods provide mass selectivity, but not elemental selectivity e.g., isobars cannot be distinguished.

Another of the recognized problems of the SIMS method is the relatively small quantity of secondary ions that are produced during the bombardment of the sample. Accordingly, it is relatively difficult to determine extremely small numbers of atoms of the desired specie. In addition, quantitative measurements with SIMS are difficult and may be unreliable due to chemical and physical matrix effects which severely affect the secondary ion yield. Furthermore, since various gaseous environments are frequently used to assist in the production of secondary ions, the SIMS method is not applicable to measuring the atoms that also comprise the added environment.

Thus, it is desirable to provide an analytical method having a high sensitivity and selectivity, and which is suitable for a greater number of samples than these prior art methods.

Accordingly, it is an object of the present invention to provide a method of sputtering material from the surface of a sample and thereafter ionizing by RIS the specific component of interest from the resultant sputtered material, and detecting these ions as a measure of the concentration of the selected component in the sample.

It is another object of the invention to prevent the interference by secondary ions produced during the sputtering of material from the surface of a sample, with the detecting of the ions produced by the RIS ionization of only the neutral particles.

Also, it is an object of the invention to provide for the sputtering of material from a solid sample with an ion beam that is well defined both in composition and geometrical dimensions and thereafter uniquely ionizing resultant neutral particles of the component of interest in the analysis using resonance ionization spectroscopy, and detecting these ions as a measure of the concentration of that component.

A further object of the invention is to provide apparatus for the carrying out of the methods of the above-stated objects.

In addition, it is an object of the invention to provide apparatus for directly detecting the ions produced by resonance ionization spectroscopy, or for detecting these ions after (with or without energy filtering) time-of-flight analysis, quadrupole filter mass analysis, mass analysis, and/or other magnetic mass or spectrographic analysis.

Disclosure of the Invention

In accordance with the invention, apparatus and a method of operating the apparatus are provided for the sensitive and selective analysis of a specific component in a sample. The sample is subjected to bombardment of energetic particles, such as ions, thereby producing a cloud containing neutral particles and secondary ions of constituents within the sample. The secondary ions can be separated from the neutral particles, and the remaining neutral particles are then subjected to photons from a laser system having the appropriate wave lengths for the selective ionization of neutral particles of the desired elemental specie. Alternately, all of the sputtered material may be subjected to ionization by RIS. The ions created from the selected specie can be treated in several ways in order to measure the concentration of the component in the sample. Specific of these treatments include direct measurement, time-of-flight mass analysis, r-f quadrupole mass analysis and magnetic mass analysis. If desired, even the isotopic species of the component can be selected for final analysis by the last three named treatments.

BEST MODE FOR CARRYING OUT THE INVENTION

Figure 1:
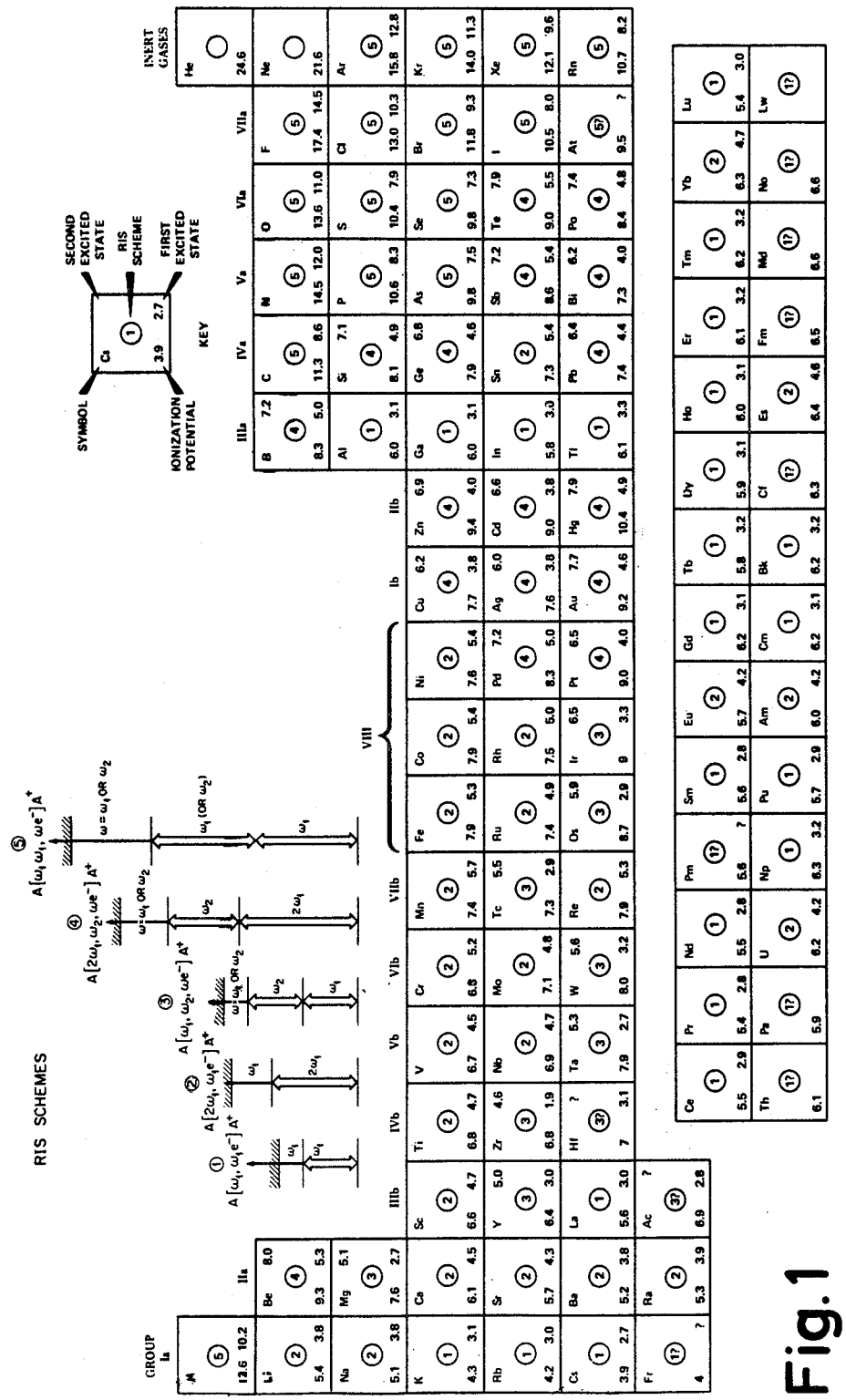
FIG. 1 is a chart showing the elements of the periodic table and various possible resonance ionization spectroscopy schemes that are appropriate for the selective ionization of these elements.

Referring to FIG. 1, shown therein is a chart of the elements of the periodic table. Within each block is indicated the symbol of the element, the energy of the first excited state, the energy of the second excited state (if such is used) and the ionization potential for the element. Furthermore, in the center of each block is designated the particular resonance ionization spectroscopy scheme that may be used to produce ionization of that element.

Above the chart are shown those specific RIS schemes. In Scheme 1, used for example with potassium, a photon of a selected wavelength is used to raise an electron in an atom from the ground state up to the first excited state. A second photon of the same wavelength then produces ionization of the atom. Similarly for Scheme 3, a photon of a first wavelength excites an atom from its ground state to a first excited state. A photon of a second wavelength further excites the atom to a second excited state, and another photon of either of the wavelengths then completes the ionization process. This Scheme 3 may be used for producing ions of zirconium, for example. All of the elements of the periodic table, except helium and neon, may be analyzed by using one of the five RIS schemes by employing commercial lasers.

Figure 2:
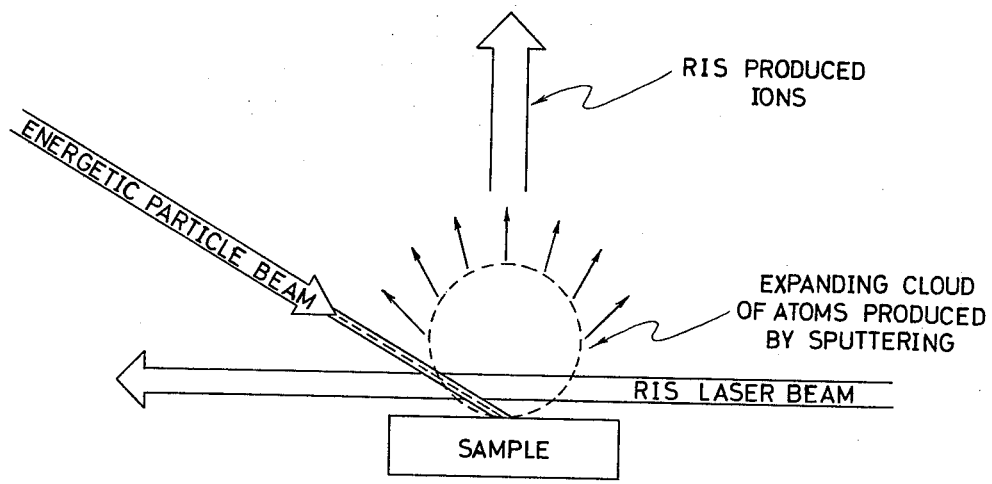
FIG. 2 is a schematic drawing illustrating the principles of the present invention.

Shown in FIG. 2 is the basic principle of the present invention. According to the invention, a sample, which may be either solid or liquid, is bombarded with energetic particles. The energetic particles may be, for example, ions (including electrons) or neutral particles. If the particles have sufficient energy, a cloud of sputtered material will be formed adjacent the surface of the sample. This cloud will contain both charged and neutral particles of substantially all constituents of the sample. The cloud is then subjected to the passage therethrough of one or more laser beams tuned to produce light of wavelengths corresponding to those needed to produce RIS ionization of a particular component of the cloud. The RIS ions thus produced correspond to the component within the sample for which an analysis is desired, and the quantity of these ions can be related to the concentration of that component in the sample.

Figure 3:
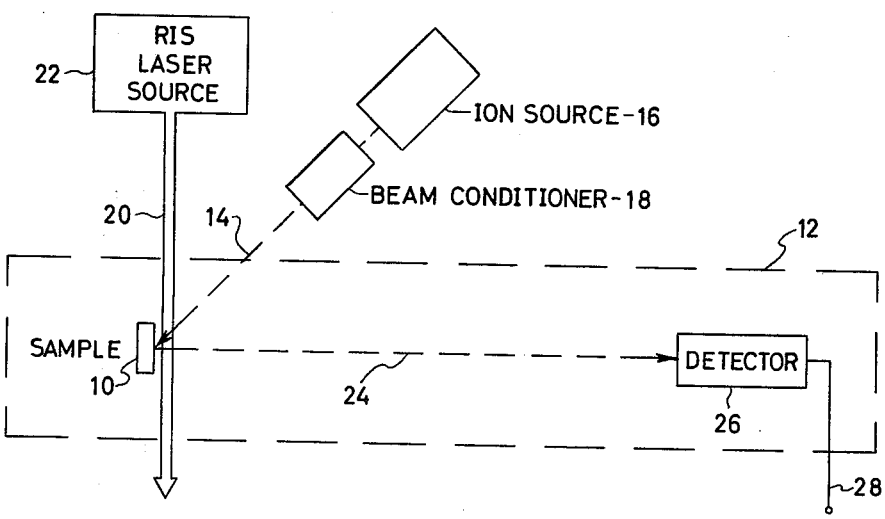
FIG. 3 is a schematic drawing illustrating the principles of the present invention, i.e., sputter initiated resonance ionization spectroscopy, using direct detection of RIS produced ions.

Referring now to FIG. 3, shown therein are the basic components and principles required for the carrying out of the present invention. A sample 10 of the material to be investigated is mounted appropriately within an evacuated container 12. The particular pressure (vacuum) required for the carrying out of the invention will be described in more detail hereinafter. The sample 10 is bombarded with, in this instance, an ion beam 14 as derived from an ion source 16. Since an ion source may produce ions of other materials than those desired for the beam 14, a magnetic mass filter as one component of beam conditioning apparatus 18 can be utilized to remove the extraneous ions. The ion beam 14, upon striking the sample 10, causes the release of a cloud containing, for example, secondary ions and neutral atoms from the sample. Not shown in this drawing are means for suppressing the secondary ions and leaving the neutral particles for the subsequent analysis steps if this suppression is desired. After the suppression of these secondary ions, a laser beam 20 derived from a RIS laser source 22 is passed through the neutral particles whereupon those materials which correspond to the RIS photon wavelength(s) are ionized. These RIS-produced ions, indicated with the ion beam 24 in the drawing, then impinge upon an appropriate ion counter 26 giving rise to an electrical signal on lead 28. Also, not shown herein (or in FIGS. 4–7) are means for accelerating and/or focusing the RIS-produced ions toward the detector.

Figure 4:
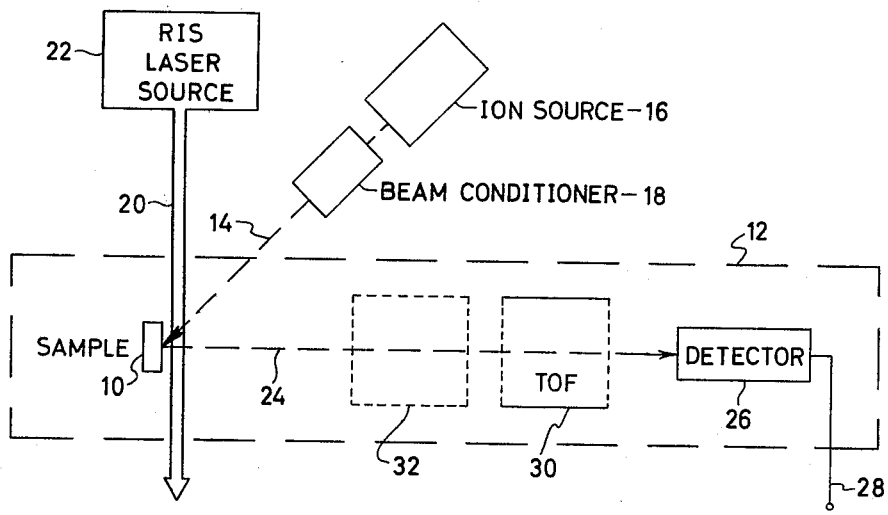
FIG. 4 is a schematic drawing illustrating the principles of the invention using a time-of-flight spectrometer prior to detection of the ions.

Although RIS involves the ionization of atoms of a specific element or molecule through the choice of the laser wavelength, spurious ions having different masses may be produced in some particular applications. These may be a small number of ions of other elements which are present in much greater abundance than the element to be detected. State of the art lasers can be used to discriminate isotopes of a given element, but only in certain special cases. On the other hand, it is often generally desired to select ions of a particular mass from the variety actually produced. Thus, incorporated into this invention is the use of a variety of mass spectrometers. One of the simplest ways to obtain information on the mass of an ion is by using a time-of-flight mass spectrometer. This is illustrated in FIG. 4. As in FIG. 3, an ion beam 24 that contains predominantly ions of a single element is created by use of RIS on neutral particles generated from a sample 10. These ions are then passed through a time-of-flight spectrometer (TOF) 30 prior to impingment upon the detector 26. A determination of the time between generation of the ions and their arrival at the detector identifies the specific mass(es) of the ion(s) giving rise to the signal(s) on lead 28 thus reducing effects due to spurious ionization in the RIS process. Further, the use of RIS to select the Z (atomic number) of an atom, and a mass spectrometer to select the A (atomic mass) of an atom, gives both Z and A selection on the same atom. For example, isobars in atoms with the same A, but a different Z can be separated in this manner.

Ions produced via the RIS of sputtered atoms may have a relatively wide energy range. Thus, for any type of mass analysis, an energy filter 32 may be inserted into the ion beam 24 prior to the mass analyzer, in this case, the TOF 30. Such an energy filter may also be utilized with the possible variations shown in FIGS. 5, 6 and 7.

Figure 5:
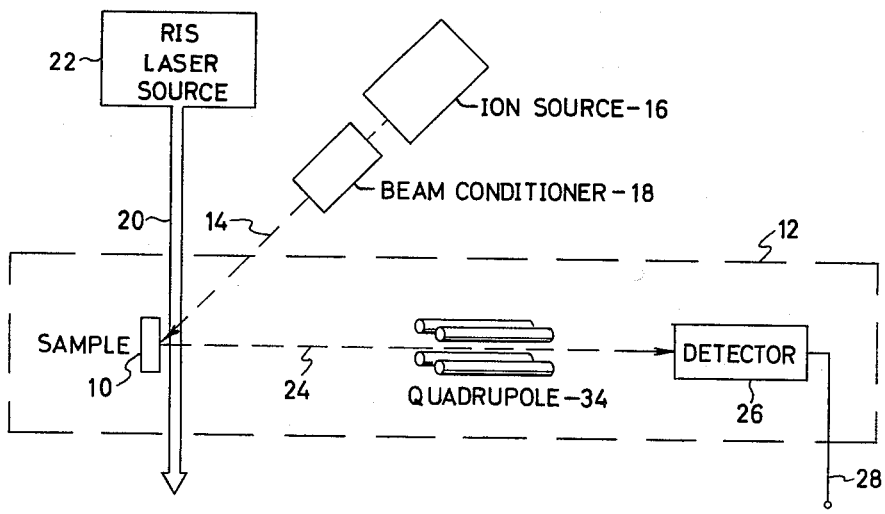
FIG. 5 is a schematic drawing illustrating the principles of the present invention using a r-f quadrupole mass spectrometer.

Another method of obtaining information as to the mass of the ion is through use of an r.f. quadrupole mass spectrometer 34 as shown in FIG. 5. Use of a quadrupole provides certain advantages over a TOF analyzer when it is desired to keep the ion energy low, and when better mass selection is needed.

Figure 6:
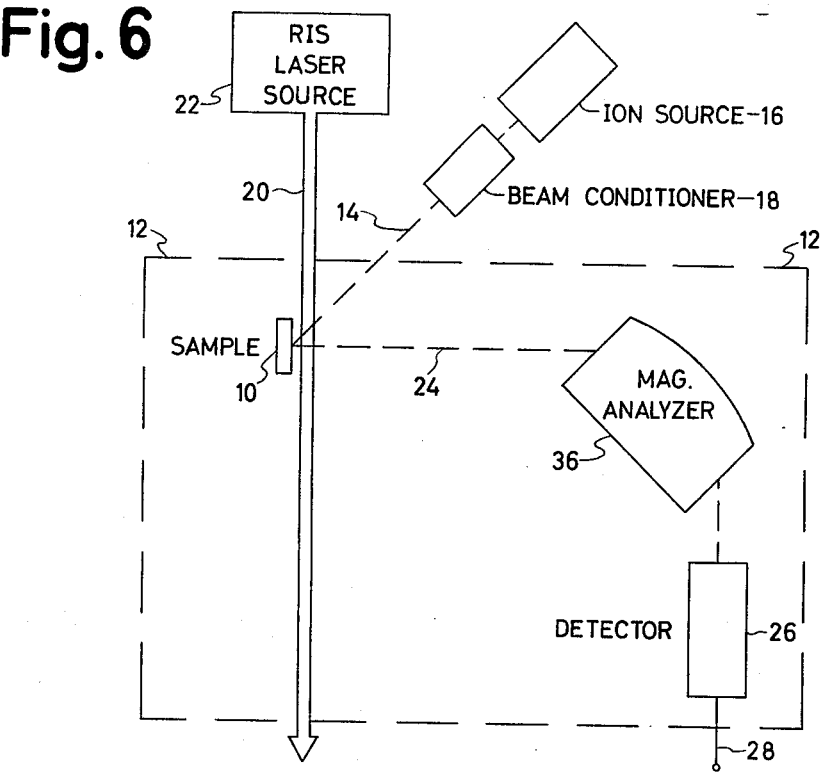
FIG. 6 is a schematic drawing illustrating the principles of sputter initiated resonance ionization spectroscopy using a magnetic sector mass spectrometer.

Shown in FIG. 6 is another means of mass analysis using a magnetic sector mass spectrometer 36 interposed in the ion beam ahead of the detector 26. A magnetic analyzer has the advantages of a very high efficiency (high throughput) and an abundance sensitivity that can be as high as $10^6$ or $10^7$. Thus, additional mass discrimination is achieved.

Figure 7:
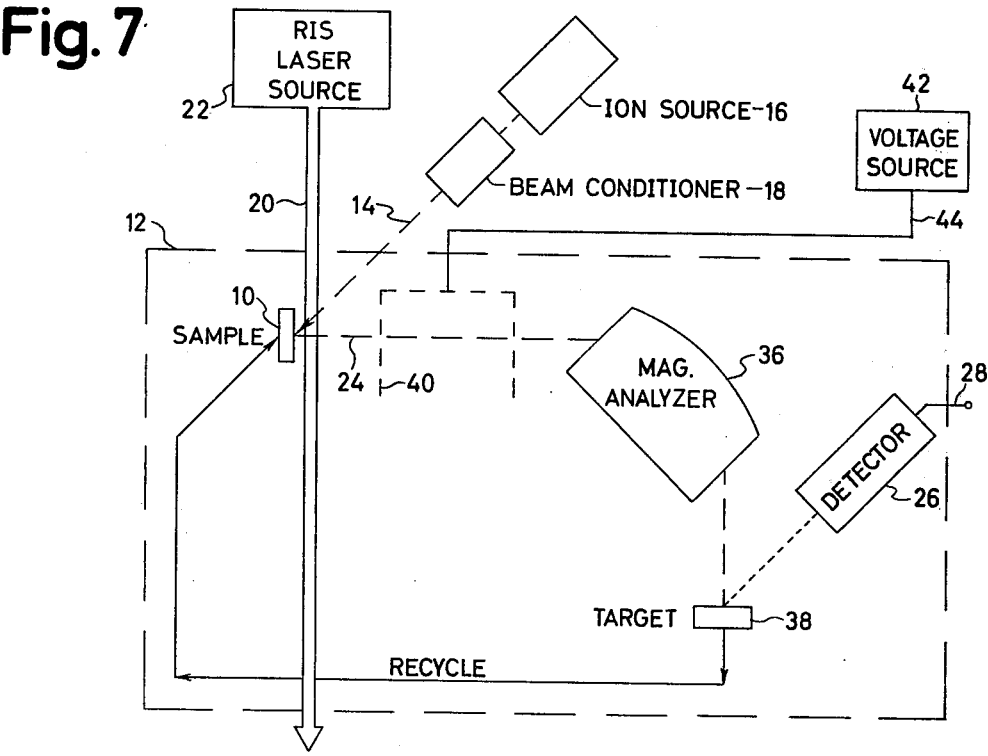
FIG. 7 is a schematic drawing illustrating the principles of the invention as shown in FIG. 6 and the principle of enriching the selected component, or an isotope thereof, in a sample for increased selectivity.

A further modification of the means of mass analysis shown in FIG. 6 is illustrated in FIG. 7. Shown therein is a principle of achieving substantially increased abundance sensitivity. Ions, after passing through the sector magnet 36, are imbedded into a target 38. To achieve incorporation of the ions into the target, an additional acceleration of the ions must be achieved. This can be accomplished by acceleration grids 40 supplied with appropriate voltage(s) from a voltage source 42 through lead 44. During implantation the detector 26 measures electrons emitted from the target.

After a substantial fraction of the component of interest in the sample is removed, ionized, and incorporated into the target, this target may be recycled to the sample position. The specie of interest may then be reionized, and the ions again passed through the magnetic mass spectrometer. If the abundance ratio of the mass spectrometer is $10^6$, two passes will give a discrimination of neighboring masses (e.g. isotopes) of $10^{12}$; and after n cycles through the spectrometer, a selectivity between adjacent masses is about $10^{6n}$.

Figure 8:
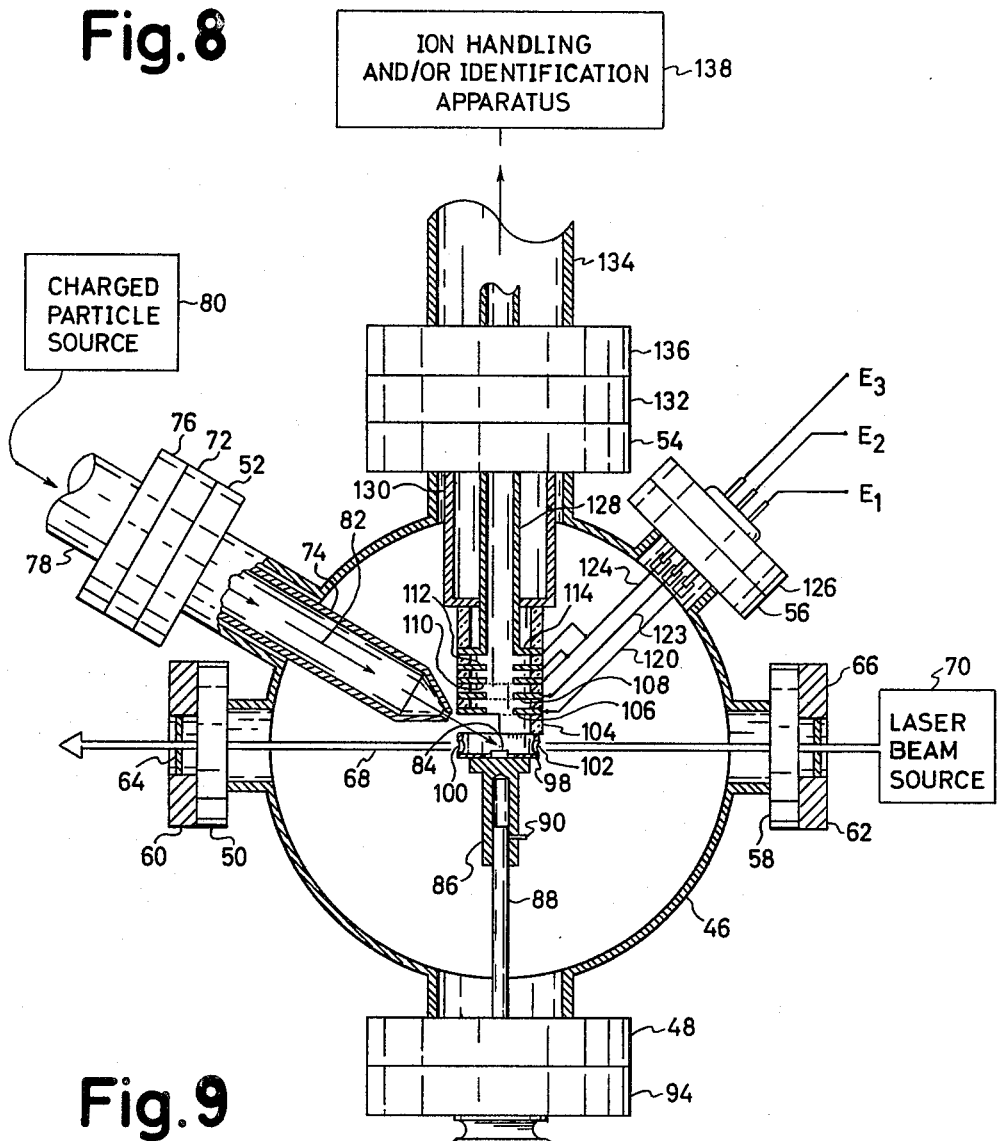
FIG. 8 is a schematic drawing of typical apparatus for carrying out the present invention.

While the foregoing illustrates the basic principles of the invention, exemplary apparatus for carrying out the invention is illustrated in FIG. 8. This is a top cross-sectional view of an analysis vessel 46 which can be provided, for example, with a plurality of flanged ports 48–58 for purposes hereinafter described. Attached to ports 50, 58 are flanges 60, 62 each containing a laser beam penetratable window 64, 66 whereby a laser beam 68 from a source 70 may be passed through the vessel 46. The source 70 can include means for pulsing the laser beam if desired. Mounted upon port 52 is a flange 72 or other suitable support for a grounded collimating tube 74 leading into the vessel 46. Also attached at port 52 is a flange 76 or other suitable connection for a transport tube 78 leading from a charged particle source 80. This source 80 gives rise to a charged particle beam 82 passing through the transport tube 78 and collimator 74. Included in the transport tube 78 and/or the source 80 can be means (not shown) for the focusing and/or pulsing of the charged particle beam 82.

A sample 84 is positionable proximate the path of the laser beam 68 with any suitable mechanism. In this view, the sample 84 is at the end of sample support 86 which, in turn, is mounted from a rod 88 using an appropriate fastener 90, for example. The rod 88 passes through an insulator 92 in flange 94 attached to port 48, and the terminal end 96 of the rod 88 is available for the application of a potential $E_4$, if desired.

Figure 9:
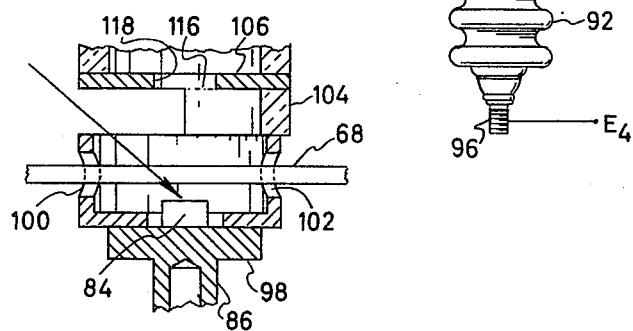
FIG. 9 is an enlarged view of a portion of the apparatus of FIG. 8.

As shown also in FIG. 9, when the sample 84 is in position for analysis, it is within the base of a Faraday cage 98 having opposed apertures 100, 102 for the passage of the laser beam 68 therethrough. The cage 98 can be supported from an insulator 104. This can be supported, in turn, on the end of a group of electrodes 106–114 each separated from each other with appropriate insulators. Electrode 106 can be provided with a grid 116 in the aperture 118 thereof to properly contain the electrical field produced by this electrode. Similar grids can be positioned in electrodes 108 and 110 for the same purpose. Appropriate potentials $E_1$, $E_2$, $E_3$ can be applied to electrodes 106–110 via leads 120–124, respectively, which pass through an appropriate flange 126 attached to port 56. In the embodiment shown, electrodes 112 and 114 are operated at the same potential ($E_3$) as electrode 110.

The electrode 114 is attached to an inner end of a field-free drift tube 128. This tube 128 is within a grounded support sleeve 130 attached to port 56 with a flange 132 or other suitable means. The outer end of the drift tube 128 passes through a conduit 134 which may be mounted from flange 136, for example. The drift tube leads to appropriate ion handling and/or identification apparatus 138 such as a mass analyzer and/or a detector.

In a normal operation of the apparatus illustrated in FIG. 8, a beam of energetic particles, such as electrons, positive ions, etc., is produced at the source 80 and caused to pass through the collimator 74 to strike the sample 84. This beam produces, adjacent the surface of the sample, a cloud of sputtered material which includes both ions and neutral particles. As discussed above, the passage of an appropriate laser beam (or beams) 68 through this cloud produces selected ions corresponding to the element(s) for which the wavelength(s) of the laser beams are chosen for RIS. The RIS ions are withdrawn into the drift tube 128 using appropriate potentials on the electrodes 106–114. If the ions produced during sputtering are not to be analyzed, a repelling electrical field can be produced between electrode 106 and the sample 84 (and cage 98) wherein the electrode 106 is at a more positive potential than the sample until the passage of the laser beam through the cloud.

Figure 10:
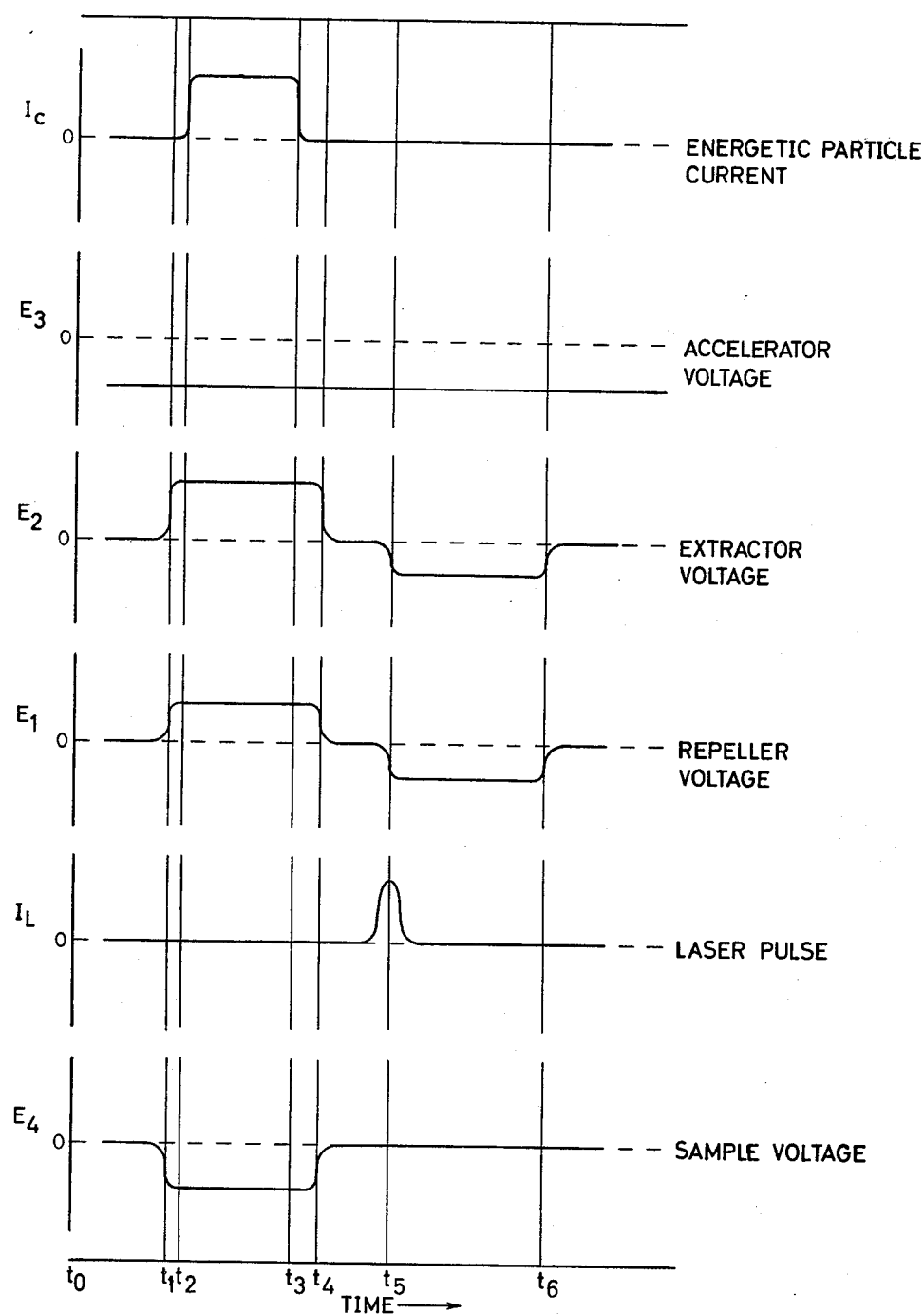
FIG. 10 is a typical plot of the time sequence of the steps involved in the subject invention.

The apparatus of FIG. 8 is primarily intended for pulsed operation, and the various steps of the method are accomplished in a time sequence. For example, a typical time graph of the method is illustrated in FIG. 10. During some initial time period, such as from $t_0$ to $t_2$, there is no energetic particle current striking the target 84. Then, from time $t_2$ to time $t_3$, the energetic particle beam 82 is permitted to strike the sample to sputter material therefrom. During approximately the same time interval, or a slightly longer time interval, e.g. $t_1$ to $t_4$, positive potentials $E_1$ and $E_2$ may be applied to electrodes 106, 108, respectively. If desired, a negative potential $E_4$ may be also applied to the sample 84 and cage 98. These potentials, when present on electrode 106 and sample 84, cause any ions produced during sputtering to be repelled toward the sample and cage.

Shortly after the completion of the charged particle pulse, the laser pulse is produced as at time $t_5$. At or near this time, the potentials $E_1$ and $E_2$ are reversed so as to extract RIS ions produced by the laser beam 68. These potentials are continued, for example, until time $t_6$, to ensure that the RIS ions are drawn into the drift tube 128. The electrode 110 (and electrodes 112, 114) may be maintained constantly at potential $E_3$ for assisting in the RIS ion extraction.

Alternatively, the electrode configuration can be altered to permit the passage of the laser beam between the repeller electrode 106 and the extractor electrode 108. This would necessitate the repositioning and/or shaping of the repeller electrode near the sample. Also, the timing sequence may then require alteration as will be recognized by those versed in the art.

Ion detectors, typically electron multiplier detectors, give rise to many spurious signals. Thus, it is necessary to discriminate between these signals and one arising from the ion of interest. One method of accomplishing this is to use a detector gating pulse slightly delayed with respect to the laser pulse. During this interval of the gating pulse, a desired output signal occurs with minimal interference.

Figure 11:
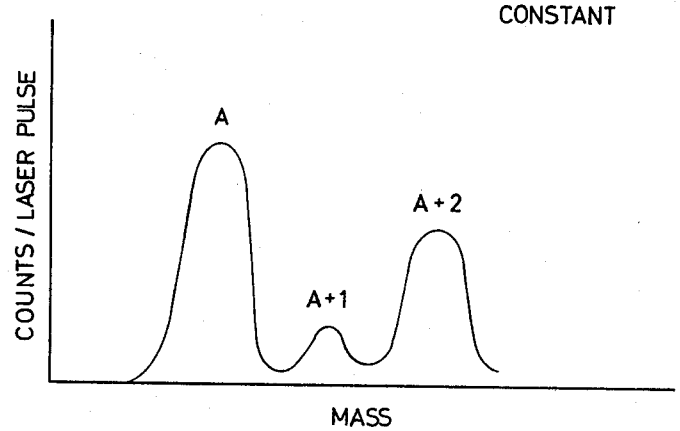
FIG. 11 is a plot illustrating the detection of isotopic species of an element in a sample by varying the magnetic field of a magnetic sector mass spectrometer according to the present invention.

The signal can be made to represent either ions of an element or the isotopes of that element. Referring to FIG. 11, for example, shown therein is an illustration of isotope identification of a particular element. As indicated for a specific atomic number, and a constant wavelength(s) laser, a plot of the counts per laser pulse as a function of mass identifies the atomic masses (i.e. isotopes) for that element, e.g., A, A+1, A+2.

Figure 12:
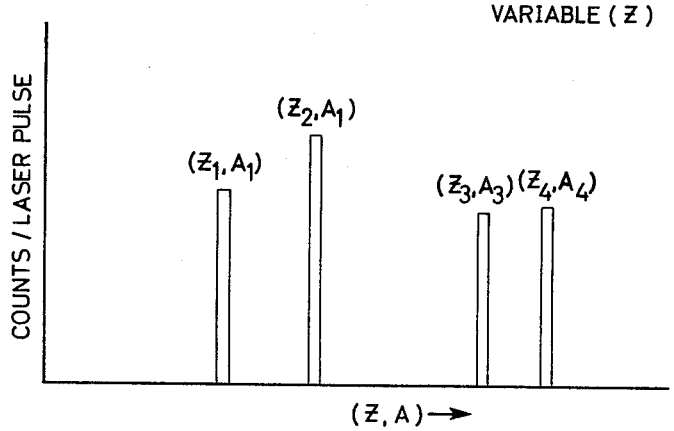
FIG. 12 is a plot illustrating the detection of specific elements in a sample by varying the wavelengths of the laser pulses and simultaneously varying the magnetic field of a magnetic mass spectrometer according to the present invention.

Alternately, for constant A, the wavelength(s) within the laser beam may be changed to discriminate isobars. In this case, the counts per laser pulse for various wavelengths identifies specific elements even in the event of isobars, e.g., $(Z_1, A_1)$ and $(Z_2, A_1)$. This is illustrated in FIG. 12 which is a bar diagram for various combinations of Z and A. The diagram also shows the more typical case where the wavelength (to specify Z) and the magnetic field (to specify A) are programmed together to compare the abundance of one species $(Z_3, A_3)$ with that of another $(Z_4, A_4)$.

The following example, describing the analysis for specific constituents of a sample, is given to further illustrate the present invention.

The impurity level of aluminum in silicon is one analysis that is accomplished using the present invention. A small chip of silicon, approximately $0.5 \times 6 \times 6$ mm is mounted on the support 86 such that it is about 1.5 cm away from the extraction electrode 106, and the vessel 46 is evacuated to a pressure of about $5 \times 10^{-8}$ Torr. The sample is then baked to a temperature of about 250° C. to outgas the sample of residual gas atoms and molecules absorbed from the previous atmospheric environment. Thereafter, the vacuum is increased to about $10^{-9}$ Torr.

A positive Ar ion beam is adjusted to produce a current of about 1 mA with an accelerating potential of about 20 kV. The ion beam is pulsed at a frequency of 10 Hz and at a rate such that a pulse of ions of 2 usec duration strike the target. During the pulse approximate $1.3 \times 10^{10}$ argon ions are focused onto the sample in a 1-2 mm diameter spot. The sputtering yields of aluminum and silicon are both about two neutral atoms per incident ion thus approximately $2.5 \times 10^{10}$ neutral atoms of silicon and a few atoms of aluminum are sputtered from the surface of the sample. The atoms are emitted in various directions in a manner as represented by a cosine distribution. The atoms are also emitted with an average energy of approximate 10 eV. The sputtered ions (silicon and aluminum) are attracted back to the target with a bias potential of approximately $-300$ volts between the target and electrode 106. Neutral atoms of sputtered silicon and aluminum are then intersected by a 1 mm diameter laser beam centered just above the sample surface.

The laser light is typically produced by a Quanta-Ray Model DCR-1A Nd:YAG and Model PDL-1 Dye Laser. The wavelength of the light produced by the laser is tuned to 3093 Å to excite a neutral atom of aluminum from the ground state to the excited state. Excited aluminum atoms are photoionized by the absorption of a second photon of wavelength 3093 Å (Scheme 1, FIG. 1). Typically, a Quanta-Ray Model DCR-lA Nd:YAG laser and a Model PDL-1dye laser using DCM dye supplied by the Exciton Chemical Company, Inc., and a 58° KD*P frequency doubling crystal supplied by Quanta-Ray, produces the 3093 Å light with an energy per pulse of 10 millijoules. When this light energy is concentrated into a 1 mm diameter beam, this is equivalent to a photon fluence of $2 \times 10^{18}$ photons/cm$^2$ which is much more than enough to meet the saturation condition. The laser beam is pulsed on about 2.5 usec after the initiation of the ion beam. This time permits movement of both fast and slow neutral aluminum atoms into the laser beam.

For the case of aluminum, the laser will ionize about 1% of the atoms in the selective RIS process. Assuming that all of the ions will be transmitted through the system, and using 6000 laser pulses, one atom of aluminum in $10^{10}$ atoms of silicon can be measured to plus or minus 10%. Where additional sensitivity and/or precision is desired, the number of laser pulses can be increased.

As stated above, the method described with regard to the apparatus of FIG. 8 is a pulsed mode method. It is pulsed in two respects; namely, the pulsing of the ion beam striking the sample, and the pulsing of the laser beam. In some analyses, it may be desirable to determine the composition with regard to a particular element at the surface of a sample and thereafter at various depths within the sample. This may be accomplished with the apparatus described herein by first pulsing the ion beam, and through the use of a pulsed laser beam, making an analysis of the composition at the surface. Thereafter, the ion beam may be made to impinge upon the sample for a longer duration and/or with a higher frequency thereby permitting the sputtering away of a portion of the surface. This then permits the analysis for the particular constituent to be repeated at a depth beneath the surface, a technique which is referred to as depth profiling.

There have been described herein what are presently considered to be the preferred embodiments of this invention, both in apparatus and in method of operation. It will be recognized by those skilled in the art that various changes and modifications may be made therein without departing from the invention. Accordingly, the scope of the invention should be defined only by the appended claims and the equivalence thereof.

What is claimed is:

1. A method of quantitatively analyzing for a component in a sample, said method having sufficient sensitivity to determine as little as one atom, which comprises:
    bombarding said sample with energetic particles thereby producing a cloud of constituents of said sample;
    subjecting said cloud to laser initiated resonance ionization spectroscopy for selectively ionizing constituents in said cloud corresponding to said component; and
    accurately and substantially simultaneously detecting said ions resulting from said laser initiated resonance ionization spectroscopy as a measure of the quantity of said component in said sample with said sensitivity.

2. The method of claim 1 wherein said cloud includes ions and neutral particles, and further comprises removing said ions from said cloud prior to said laser initiated resonance ionization spectroscopy step.

3. The method of claim 1 wherein said energetic particles comprises a beam of energetic ions.

4. The method of claim 1 further comprising subjecting said ions resulting from said laser initiated resonance ionization spectroscopy to mass analysis prior to said detecting step.

5. The method of claim 4 wherein said mass analysis comprises passing said ions through a time of flight mass spectrometer.

6. The method of claim 4 wherein said mass analysis comprises passing said ions through an r.f. quadrupole mass spectrometer.

7. The method of claim 4 wherein said mass analysis comprises passing said ions through a magnetic sector mass spectrometer.

8. The method of claim 4 further comprising imbedding ions after said mass analysis step into a target during said detecting step, and recycling said target as said sample for repeating said analysis.

9. The method of Claim 3 wherein said bombarding ion beam comprises positive argon ions.

10. The method of claim 1 wherein said bombarding energetic particles comprises a beam that is repetitively pulsed.

11. The method of claim 10 wherein said laser beam for achieving resonance ionization spectroscopy is repetitively pulsed in a selected time relationship with the frequency of said energetic particle beam.

12. The method of claim 2 wherein the removing of said ions from said cloud is accomplished by maintaining a more negative potential upon said sample than on a first electrode adjacent said sample.

13. The method of claim 5 further including passing ions produced by said laser beam initiated resonance ionization through an energy filter prior to subjecting said ions to said mass analysis.

14. The method of claim 5 further comprising applying a potential to a second electrode adjacent said first electrode, and more removed from said sample than said first electrode, for accelerating said ions produced by said laser initiated resonance ionization.

15. The method of claim 14 wherein said laser initiated resonance ionization spectroscopy ionization step is carried out between said first electrode and said sample.

16. The method of claim 14 wherein said laser initiated resonance ionization spectroscopy ionization step is carried out between said first electrode and said second electrode.

17. The method of claim 1 wherein said detecting of said ions of said specific component is achieved in an electron multiplier detector.

18. Apparatus for the quantitative analysis of a component in a sample, said analysis having sufficient sensitivity to determine as little as one atom of said component, which comprises:
   means for mounting said sample;
   a source of energetic particles of sufficient energy to sputter material from said sample to form a cloud of sputtered constituents of said sample;
   means for directing said energetic particles onto said sample thereby creating said sputtered cloud of said constituents in said sample;
   a laser beam source tuned to produce a beam of photons of selective wavelengths capable of producing ions by resonance ionization spectroscopy of a selected component within said cloud;
   means for directing said selected photons from said laser source to intercept said cloud and thereby selectively ionize said selected component; and
   detector means for accurately and substantially simultaneously measuring said ions produced by said resonance ionization spectroscopy as a measure of the quantity of said component with said sensitivity.

19. The apparatus of claim 18 wherein said source of energetic particles is a source of an energetic ion beam.

20. The apparatus of claim 18 further comprising means for separating ions produced by said energetic particles from said cloud.

21. The apparatus of claim 20 wherein said means for separating ions comprises a first electrode adjacent said sample mounting means, said first electrode maintained at an electrical potential relative to said sample to repel said ions toward said sample.

22. The apparatus of claim 21 further comprising an accelerating means adjacent said first electrode, and more removed from said sample mounting means than said first electrode, for accelerating said ions of said resonance ionization spectroscopy toward said detector means.

23. The apparatus of claim 22 wherein said accelerating means comprises a second electrode means maintained at an electrical potential sufficient for said acceleration.

24. The apparatus of claim 19 wherein said ion source produces a beam of positive ions of argon.

25. The apparatus of claim 24 further comprising means for pulsing said ion beam from said source prior to directing said ions from said ion source upon said sample.

26. The apparatus of claim 25 further comprising means for pulsing said beam of photons at a frequency in a timed relationship to said pulses of said ion beam.

27. The apparatus of claim 18 wherein said means for said ions of said component in said sample comprises an electron multiplier detector.

28. The apparatus of claim 18 further comprising an energy filter, interposed between said sample mounting means and said detector, for receiving said ions produced by said resonance ionization spectroscopy to achieve energy discrimination of said ions of said resonance ionization spectroscopy.

29. The apparatus of claim 28 further comprising a mass analyzer attached to the output of said energy filter for the mass discrimination of said ions produced by said resonance ionization spectroscopy.

30. The apparatus of claim 29 wherein said mass analyzer is a time of flight mass spectrometer.

31. The apparatus of claim 29 wherein said mass analyzer is an r.f. quadrupole mass analyzer.

32. The apparatus of claim 29 wherein said mass analyzer is a magnetic sector mass analyzer.

* * * * *